(12) United States Patent
Pratley

(10) Patent No.: US 6,335,000 B1
(45) Date of Patent: Jan. 1, 2002

(54) HAIR STYLING COMPOSITION

(75) Inventor: Stuart Keith Pratley, Wirral (GB)

(73) Assignee: Unilever Home & Personal Care USA, division of Conopco, Inc., Chicago, IL (US)

(*) Notice: Subject to any disclaimer, the term of this patent is extended or adjusted under 35 U.S.C. 154(b) by 0 days.

(21) Appl. No.: 09/543,197

(22) Filed: Apr. 5, 2000

(30) Foreign Application Priority Data

Apr. 7, 1999 (GB) .................................. 9907954

(51) Int. Cl.⁷ .............................. A61K 9/00; A61K 7/06; A61L 9/04
(52) U.S. Cl. ............................. 424/47; 424/45; 424/70.1; 424/70.11; 424/70.12
(58) Field of Search .............................. 424/70.1, 47, 45, 424/70.11, 70.12, 70.21, 70.22, 70.27, 70.31; 514/63

(56) References Cited

U.S. PATENT DOCUMENTS 6,001,339 A * 12/1999 Finel et al.
5,776,444 A 6/2000 Birtwistle et al.
2001/0009659 * 7/2001 Pratley et al.

FOREIGN PATENT DOCUMENTS

| EP | 0445982 | 9/1991 |
| EP | 0818190 | 1/1998 |
| WO | 00/21493 | 4/2000 |
| WO | 00/33797 | 6/2000 |

OTHER PUBLICATIONS

Search Report under Section 17, Application No. GB 9907954.3 dated Jun. 22, 1999.
International Search Report Application No. PCT/EP 00/02392 mailed Aug. 16, 2000.

* cited by examiner

Primary Examiner—Thurman K. Page
Assistant Examiner—Brian K. Seidleck
(74) Attorney, Agent, or Firm—Matthew Boxer

(57) ABSTRACT

The invention provides hair styling compositions, for example creams, gels and especially aerosol hair styling mousses. The compositions contain a cross-linked silicone, such as an emulsion of cross-linked dimethiconol gum, and a cationic hair styling polymer having a cationic charge density of at least 1 meq/g. The compositions provide excellent styling as well as sensory feel.

8 Claims, No Drawings

HAIR STYLING COMPOSITION

FIELD OF THE INVENTION

The present invention relates to hair styling compositions, for example creams, gels and especially aerosol hair styling mousse compositions, which contain cross-linked silicone and which deliver excellent styling as well as sensory feel.

BACKGROUND AND PRIOR ART

Style creation products such as hair styling mousses provide human hair with a temporary set which can be removed by water or by shampooing, and function by applying a thin film of a resin or gum onto the hair to adhere adjacent hairs together so that they retain the particular shape or configuration at the time of application.

EP 818 190 describes how an emulsion polymerised silicone material having a particular, defined level of cross-linking, and which is cross-linked in emulsion form can be incorporated into a hair styling composition, such as a mousse, gel or cream, to give a formulation which delivers excellent style creation and longevity, whilst leaving the hair soft and natural. An important feature of these systems is the phase behaviour of the silicone, which is said to form a separate high viscosity aggregated phase in the composition. This phase behaviour is considered to be key to effective style creation.

A problem with "aggregating" systems as described in EP 818 190 is that they can tend to gel and form lumps under conditions of prolonged, high temperature storage.

One solution to this problem is to use a nonionic surfactant having an HLB value of at least 14.5, such as those nonionic surfactants of general formula R(EO)x H, where R represents a straight or branched chain alkyl group having an average carbon chain length of 12–18 carbon atoms and x ranges from 30 to 50.

However, some of the above-described nonionic surfactants form particularly stable foams. In the case of hair styling mousse product forms, consumers generally prefer that the foam generated collapses after less than five minutes after discharge, for ease of spreading on the hair. In such instances, this necessitates the use of anti-foaming ingredients in the composition to reduce foaming to a consumer-acceptable level.

Surprisingly, it has now been found that by the use of certain cationic polymers of specified cationic charge density, the silicone materials as described in EP 818 190 may be formulated into systems which do not form a separate high viscosity aggregated phase and yet nevertheless deliver effective style creation. Advantageously, it is not necessary to use high HLB nonionic surfactants with these systems, which allows the formulator greater freedom to formulate the a composition with the desired foam properties.

SUMMARY OF THE INVENTION

The present invention provides a hair styling composition comprising:
 (i) from 0.1% to 10% by weight, based on total weight, of a cross-linked silicone polymer, in which the percentage of branched monomer units in the silicone polymer is from 0.05% to 10%;
 (ii) from 0.1% to 10% by weight, based on total weight, of a cationic hair styling polymer having a cationic charge density of at least 1 meq/g;
 (iii) from 0.01% to 5% by weight, based on total weight, f a surfactant;
 (iv) water; and
 (v) from 0% to 30% by weight, based on total weight, of an aerosol propellant.

DETAILED DESCRIPTION

Cross-linked Silicone Polymer

The hair styling composition of the invention comprises a cross-linked silicone polymer (i). The silicone polymer will generally be insoluble in the aqueous medium of the hair styling composition and so be present in an emulsified form, with the silicone polymer present as dispersed particles.

Suitable cross-linked silicone polymers include cross-linked polydiorganosiloxanes, in particular cross-linked polydimethylsiloxanes (also termed cross-linked dimethicone). Also suitable for use in hair treatment compositions of the invention are cross-linked polydimethyl siloxanes having hydroxyl end groups (also termed cross-linked dimethiconol).

The cross-linked silicone polymer is present in compositions of the invention in an amount from 0.1% to 10% by weight based on the total weight of the composition, more preferably from 0.2% to 6% by weight, most preferably from 0.5 to 5% by weight.

The degree of cross-linking of the cross-linked silicone polymer can be measured as the percentage of branched monomer units in the silicone polymer. This value may suitably range from about 0.001% to about 35%, preferably 0.002 to 10%, more preferably 0.003 to 10%, optimally 0.004% to 2%. Increasing cross-linking is found to improve hair styling benefits but also to reduce conditioning performance somewhat, so compromise levels must be selected with properties optimised to suit consumer preferences in different cases. Good overall performance has been obtained with about 0.6% degree of cross-linking (i.e., percentage of branched monomer units)

Cross linking of the silicone polymer may for example be introduced in situ during the polymerisation process which forms the silicone polymer from its constituent monomer units, through the inclusion of the required amount of trifunctional and tetrafunctional silane monomer units, for example, those of formula $R\,Si\,(OH)_3$ wherein R represents an alkyl, alkenyl (e.g. vinyl), alkaryl, aralkyl or aryl (e.g. phenyl) group, preferably methyl.

Alternatively, other types of silicone cross-linking chemistry may be used to produce suitable cross-linked silicone polymers for use in the invention. The cross-linking agents employed in such methods may be organosilicon cross-linking agents, for example as listed in EP 0 473 039, or non-silicone cross-linking agents, for which a representative example is the cross-linked silicone polymer described in U.S. Pat. No. 5,654,362. The cross linker used here is an alpha, omega aliphatic diene of the following structure: $CH_2=CH(CH_2)_xCH=CH_2$, where X ranges from 1–20. A gel is formed by cross-linking and addition of Is-H across double bonds in the alpha, omega-diene.

Further examples of suitable cross-linked silicone polymers for use in the invention include the materials DC 3-2365, ex Dow Corning, and the silicone-urethane copolymer Polyderm PPI-SI-100, ex Akzo Incorporated, Matawan, N.J.

The especially preferred cross-linked silicone polymers for use in compositions of the invention are silicone gums having a slight degree of cross-linking as described in WO 96/31188. These materials can impart fullness, body and volume to hair, as well as good wet and dry conditioning.

Various methods of making emulsions of particles of cross-linked silicone polymers for use in the invention are available and are well known and documented in the art. For example, emulsions may be prepared by high shear mechanical mixing of the silicone polymer and water, or by emulsifying the silicone polymer with water and an emulsifier (mixing the silicone polymer into a heated solution of the emulsifier for instance), or by a combination of mechanical and chemical emulsification. For certain materials such as the cross-linked silicone polymer described in U.S. Pat. No. 5,654,362, it may be advisable to mix them first with a hydrophilic or hydrophobic diluent such as PPG-2 myristyl ether propionate or cyclomethicone, in order to facilitate the subsequent emulsification step.

A particularly suitable technique for preparation of emulsions of particles of silicone polymers is emulsion polymerisation. Emulsion polymerised silicone polymers as such are described in U.S. Pat. No. 2,891,820 (Hyde), U.S. Pat. No. 3,294,725 (Findlay) and U.S. Pat. No. 3,360,491 (Axon).

Suitable emulsion polymerised cross-linked silicone polymers are commercially available or can be readily made using conventional techniques well known to those skilled in the art.

Suitable cross-linked silicone polymer emulsions for use in the invention are commercially available in a pre-emulsified form. This is particularly preferred since the pre-formed emulsion can be incorporated into the hair treatment composition by simple mixing. Pre-formed emulsions are available from suppliers of silicone oils such as Dow Corning, General Electric, Union Carbide, Wacker Chemie, Shin Etsu, Toshiba, Toyo Beauty Co, and Toray Silicone Co.

The preferred cross-linked silicone gums for use in compositions of the invention are also available in a pre-emulsified form, which is advantageous for ease of formulation. An especially preferred example is the material available from Dow Corning as DC X2-1787, which is an emulsion of cross-linked dimethiconol gum in which the viscosity of the silicone polymer itself is about $2 \times 10^7$ cst.

When the cross-linked silicone polymer is incorporated as a pre-formed emulsion as described above, the exact quantity of emulsion will of course depend on the concentration of the emulsion, and should be selected to give the desired quantity of silicone polymer in the final composition.

Cationic Hair Styling Polymer

The cationic hair styling polymer (ii) employed in compositions of the present invention should be capable of forming a film and holding the hair of the user in place. It is present in compositions of the invention in an amount from 0.1% to 10% by weight based on the total weight of the composition, more preferably from 0.1% to 5% by weight, most preferably from 0.2 to 4% by weight.

Hair styling polymers are well known articles of commerce and many such polymers are available commercially which contain functional groups which render the polymers cationic, anionic, amphoteric or nonionic in character.

As used herein the "charge density" of the cationic hair styling polymer is defined as the number of cationic sites per polymer gram atomic weight (molecular weight), and is expressed in terms of meq/gram of cationic charge (meq/g). The charge density can be controlled and adjusted in accordance with techniques well known in the art. Those skilled in the art will recognise that the charge density of amino-containing polymers may vary depending upon pH and the isoelectric point of the amino groups. In general, adjustment of the proportions of amine or quaternary ammonium moieties in the polymer, as well as pH of the composition in the case of the amines, will affect the charge density. Cationic charge density of the polymer can be determined according to the Kjeldahl Method.

The cationic hair styling polymers used herein have a cationic charge density of 1.0 meq/g and higher. Preferably the polymer has a charge density of at least 2.0 meq/g. more preferably the polymer has a charge density of at least 2.5 meq/g, such as from 2.8 to 7.5 meq/g, ideally from 2.8 to 7.0 meq/g. The charge density should be within the above limits at the pH of intended use, which will in general be from about pH 3 to about pH 9, usually from about pH 4 to about pH 8.

Examples of suitable cationic hair styling polymers are copolymers of amino-functional acrylate monomers (such as lower alkylaminoalkyl acrylate) or methacrylate monomers (such as dimethylaminoethyl methacrylate) with compatible monomers such as N-vinylpyrrolidone, vinyl caprolactam, or alkyl methacrylates (such as methyl methacrylate and ethyl methacrylate) and alkyl acrylates (such as ethyl acrylate and n-butyl acrylate).

Other suitable cationic hair styling polymers include those cationic polymers containing or derived from quaternary ammonium monomers having cyclic cationic nitrogen-containing rings (such as alkyl vinyl imidazolium). The alkyl portions of these monomers are preferably lower alkyls such as the $C_1$ to $C_3$ alkyls, more preferably $C_1$ and $C_2$ alkyls.

Preferred cationic hair styling polymers include methylvinylimidazolium chloride/vinylpyrrolidone copolymers (having the CTFA designation Polyquaternium-16), provided such copolymers have a cationic charge density of 1.0 meq/g and higher, as described above. Examples include copolymers of this type in which the weight percentage of methylvinylimidazolium chloride monomer in the copolymer is at least 10%, preferably at least 25%, most preferably at least 35% by weight based on total weight of the copolymer. These materials are commercially available from BASF AG under the LUVIQUAT tradename, as LUVIQUAT FC 370, LUVIQUAT FC 550, LUVIQUAT HM 552 and LUVIQUAT FC 905.

Also suitable are vinylcaprolactam/vinylpyrrolidone/vinylimidazolium copolymers (having the CTFA designation Polyquaternium 46) provided such copolymers have a cationic charge density of 1.0 meq/g and higher, as described above. Examples include copolymers of this type which have a vinylimidazolium monomer content of at least 25% by weight based on total weight of the copolymer. An example copolymer would have weight percentages of vinylcaprolactam monomers and vinylpyrrolidone monomers and vinylimidazolium monomers of 40%, 30% and 30% respectively, by weight based on total weight of the copolymer. Preferably, the vinylimidazolium monomer content is at least 50%, ideally around 65% by weight based on total weight of the copolymer.

Copolymers of methoimidazolinium and vinylpyrrolidone would be also be suitable (having the CTFA designation Polyquaternium 11) provided such copolymers have a cationic charge density of 1.0 meq/g and higher, as described above. Examples are copolymers of this type in which the weight percentage of methoimidazolinium monomer is at least 10%, preferably at least 33%, most preferably at least 50% by weight based on total weight of the copolymer.

Surfactant

In addition to the cross-linked silicone polymer and the hair styling polymer, the hair styling composition of the invention also includes a surfactant (iii) in an amount ranging from 0.01% to 5%, preferably from 0.01% to 1%, most preferably from 0.02% to 0.8% by weight based on total weight.

Surfactants are generally classified as nonionic, anionic, cationic, amphoteric or zwitterionic according to their ionic behaviour in aqueous solution.

Examples of nonionic surfactants are condensation products of aliphatic ($C_8$–$C_{18}$) primary or secondary linear or branched chain alcohols or phenols with alkylene oxides, usually ethylene oxide and generally having from 6 to 30 ethylene oxide groups. Other suitable nonionics include esters of sorbitol, esters of sorbitan anhydrides, esters of propylene glycol, fatty acid esters of polyethylene glycol, fatty acid esters of polypropylene glycol, ethoxylated esters and polyoxyethylene fatty ether phosphates.

Examples of anionic surfactants are the alkyl sulphates, alkyl ether sulphates, alkaryl sulphonates, alkanoyl isethionates, alkyl succinates, alkyl sulphosuccinates, N-alkoyl sarcosinates, alkyl phosphates, alkyl ether phosphates, alkyl ether carboxylates, and alpha-olefin sulphonates, especially their sodium, magnesium ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from one to 10 ethylene oxide or propylene oxide units per molecule, and preferably contain 2 to 3 ethylene oxide units per molecule.

Examples of cationic surfactants are cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, (and the corresponding hydroxides thereof), and those materials having the CTFA designations Quaternium-5, Quaternium-31 and Quaternium-18.

Examples of amphoteric and zwitterionic surfactants include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates alkyl amidopropyl hydroxysultaines, acyl taurates and acyl glutamates, wherein the alkyl and acyl groups have from 8 to 19 carbon atoms.

The surfactant in compositions of the invention is most preferably a nonionic surfactant. Such a nonionic surfactant will generally have an HLB (hydrophilic-lipophilic balance) value of about 3 to about 20. The HLB value per se and how it is calculated is described in *J.Soc.cosmet.Chem.*, 1949,1, 311. For a given nonionic surfactant, the HLB value represents the weight per cent of the hydrophilic content of the molecule divided by a factor of five.

Exemplary nonionic surfactants having an HLB value of less than 10 include laureth-2, laureth-3, laureth-4, PEG-3 castor oil, an ethoxylated nonylphenol, ethoxylated octylphenol, ethoxylated dodecylphenol or ethoxylated fatty ($C_6$ to $C_{22}$) alcohol having less than 9 ethylene oxide moieties, PEG 600 dioleate, PEG 400 dioleate, and mixtures thereof.

Exemplary nonionic surfactants having an HLB value of 10 or greater include methyl gluceth-20, methyl gluceth-10, PEG-20 methyl glucose distearate, PEG-20 methyl glucose sesquistearate, PEG-200 castor oil, $C_{11-15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-21 stearyl ether, polyoxyethylene-10 oleyl ether, polyoxyethylene-20 oleyl ether, an ethoxylated nonylphenol, ethoxylated octylphenol, ethoxylated dodecylphenol or ethoxylated fatty ($C_6$ to $C_{22}$) alcohol including at least 9 ethylene oxide moieties, polyoxyethylene-20 isohexadecyl ether, dimethicone copolyol, polyoxyethylene-23 glycerol laurate, polyoxyethylene-20 glyceryl stearate, PPG-10 methyl glucose ether, PPG-20 methyl glucose ether, polyoxyethylene-80 castor oil, polyoxyethylene-15 tridecyl ether, polyoxyethylene-6 tridecyl ether, and mixtures thereof.

Preferred nonionic surfactants for use in compositions of the invention are polysorbate 20, polysorbate 80, ethoxylated nonylphenol, steareth-20, cetosteareth-20, steareth-30, cetosteareth-30, steareth-50, and cetosteareth-50.

Surfactants selected from anionic, cationic, amphoteric and zwitterionic surfactants may suitably be used in conjunction with any of the above nonionic surfactants, to improve, for example, foaming power and/or foam stability.

Water

Compositions of the present invention will also include water, preferably distilled or deionised, as a solvent or carrier for the polymers and other components. Water will typically be present in amounts ranging from 30% to 98%, preferably from 60% to 95% by weight based on total weight.

Alcohol may optionally be employed as a co-solvent in compositions of the invention as this can enhance the performance of the styling composition. A suitable alcohol is an aliphatic straight or branched chain monohydric alcohol having 2 to about 4 carbon atoms. Isopropanol and especially ethanol are preferred. A suitable level for the alcohol is up to 20%, preferably from 5% to 15%, by weight based on total weight.

Product Form

Compositions of the invention may suitably be in aerosol form. A particularly preferred product form is an aerosol hair mousse. Aerosol hair mousse compositions are emitted from the aerosol container as a foam which is then typically worked through the hair with fingers or a hair styling tool and either left on the hair or rinsed out.

Aerosol-form compositions of the invention will include an aerosol propellant (v) which serves to expel the other materials from the container, and forms the mousse character in mousse compositions. The aerosol propellant included in styling compositions of the present invention can be any liquefiable gas conventionally used for aerosol containers. Examples of suitable propellants include dimethyl ether and hydrocarbon propellants such as propane, n-butane and isobutane. The propellants may be used singly or admixed. Water insoluble propellants, especially hydrocarbons, are preferred because they form emulsion droplets on agitation and create suitable mousse foam densities.

The amount of the propellant used is governed by normal factors well known in the aerosol art. For mousses the level of propellant is generally up to 30%, preferably from 2% to 30%, most preferably from 3 to 15% by weight based on total weight of the composition. If a propellant such as dimethyl ether includes a vapour pressure suppressant (e.g. trichloroethane or dichloromethane), for weight percentage calculations, the amount of suppressant is included as part of the propellant.

The method of preparing aerosol hair styling mousse compositions according to the invention follows conventional aerosol filling procedures. The composition ingredients (not including the propellant) are charged into a suitable pressurisable container which is sealed and then charged with the propellant according to conventional techniques.

Compositions of the invention may also take a non-foaming product form, such as a hair styling cream or gel. Such a cream or gel will include a structurant or thickener, typically at a level of from 0.1% to 10%, preferably 0.5% to 3% by weight based on total weight.

Examples of suitable structurants or thickeners are polymeric thickeners such as carboxyvinyl polymers. A carboxyvinyl polymer is an interpolymer of a monomeric mixture comprising a monomeric olefinically unsaturated carboxylic acid, and from about 0.01% to about 10% by weight of the total monomers of a polyether of a polyhydric alcohol. Carboxyvinyl polymers are substantially insoluble in liquid, volatile organic hydrocarbons and are dimensionally stable on exposure to air. Suitably the molecular weight of the carboxyvinyl polymer is at least 750,000, preferably at least 1,250,000, most preferably at least 3,000,000. Preferred carboxyvinyl polymers are copolymers of acrylic acid cross-linked with polyallylsucrose as described in U.S. Pat. No. 2,798,053. These polymers are provided by B.F.Goodrich Company as, for example, CARBOPOL 934, 940, 941 and 980. Other materials that can also be used as structurants or thickeners include those that can impart a gel-like viscosity to the composition, such as water soluble or colloidally water soluble polymers like cellulose ethers (e.g. methylcellulose, hydroxyethylcellulose, hydroxypropylmethylcellulose and carboxymethylcellulose), guar gum, sodium alginate, gum arabic, xanthan gum, polyvinyl alcohol, polyvinyl pyrrolidone, hydroxypropyl guar gum, starch and starch derivatives, and other thickeners, viscosity modifiers, gelling agents, etc. It is also possible to use inorganic thickeners such as bentonite or laponite clays.

The hair styling compositions of the invention can contain a variety of nonessential, optional components suitable for rendering the compositions more aesthetically acceptable or to aid use, including discharge from the container, of the product. Such conventional optional ingredients are well known to those skilled in the art, e.g. preservatives such as benzyl alcohol, methyl paraben, propyl paraben and imidazolidinyl urea, fatty alcohols such as cetearyl alcohol, cetyl alcohol and stearyl alcohol, pH adjusting agents such as citric acid, succinic acid, sodium hydroxide and triethanolamine, colouring agents such as any of the FD&C or D&C dyes, perfume oils, chelating agents such as ethylenediamine tetraacetic acid, and polymer plasticising agents such as glycerin and propylene glycol.

The following Examples further illustrate the preferred embodiments of the invention. All percentages referred to are by weight unless otherwise indicated.

EXAMPLES

The following Examples 1 and 2 illustrate hair styling compositions according to the invention.

Example 1

| Trade Name | Chemical Name | Raw Material Supplier | Active Ingredient |
|---|---|---|---|
| | Cross linked silicone[1] | Dow Corning | 2.0% |
| LUVIQUAT FC 550 | Polyquaternium-16[2] | BASF | 2.0% |
| Tween 80 | Polysorbate 80 | ICI Surfactants | 0.3% |
| BHT | Butylated hydroxy toluene | K&K Greef | 0.02% |
| Bronopol | 2-bromo-2-nitropropane-1,3-diol | Boots | 0.01% |
| EDTA | Ethylene diamine tetra acetic acid | BDH | 0.02% |
| | Perfume | | 0.2% |
| Deionised water | Deionised water | Local Supply | to 100% |
| EtOH B Denatured | Ethanol | BP Chemicals | up to 8% |
| CAP40 | Propane/butane | Calor | 8% |

[1]Emulsion polymerised dimethiconol containing 0.6% crosslinking, 55% aqueous emulsion.
[2]Cationic charge density of copolymer is 3.3 meq/g.

Example 2

| Trade Name | Chemical Name | Raw Material Supplier | Active Ingredient |
|---|---|---|---|
| | Cross linked silicone[1] | Dow Corning | 2.0% |
| | Polyquaternium-46[3] | | 2.0% |
| Tween 80 | Polysorbate 80 | ICI Surfactants | 0.3% |
| BHT | Butylated hydroxy toluene | K&K Greef | 0.02% |
| Bronopol | 2-bromo-2-nitropropane-1,3-diol | Boots | 0.01% |
| EDTA | Ethylene diamine tetra acetic acid | BDH | 0.02% |
| | Perfume | | 0.2% |
| Deionised water | Deionised water | Local Supply | to 100% |
| EtOH B Denatured | Ethanol | BP Chemicals | up to 8% |
| CAP40 | Propane/butane | Calor | 8% |

[3]Vinylcaprolactam/vinylpyrrolidone/vinylimidazolium copolymer in which the weight percentages of vinylcaprolactam monomers and vinylpyrrolidone monomers and vinylimidazolium monomers of 40%, 30% and 30% respectively, by weight based on total weight of the copolymer. Cationic charge density of copolymer is approx. 2.0 meq/g.

Comparative Example A

| Trade Name | Chemical Name | Raw Material Supplier | Active Ingredient |
|---|---|---|---|
| | Cross linked silicone[1] | Dow Corning | 2.0% |
| Luviquat PQ 11 | Polyquaternium-11[4] | BASF | 2.0% |
| Tween 80 | Polysorbate 80 | ICI Surfactants | 0.3% |

-continued

| Trade Name | Chemical Name | Raw Material Supplier | Active Ingredient |
|---|---|---|---|
| BHT | Butylated hydroxy toluene | K&K Greef | 0.02% |
| Bronopol | 2-bromo-2-nitropropane-1,3-diol | Boots | 0.01% |
| EDTA | Ethylene diamine tetra acetic acid | BDH | 0.02% |
| | Perfume | | 0.2% |
| Deionised water | Deionised water | Local Supply | to 100% |
| EtOH B Denatured | Ethanol | BP Chemicals | up to 8% |
| CAP40 | Propane/butane | Calor | 8% |

(4)Cationic charge density of copolymer is 0.8 meq/g.

The compositions of Examples 1 and 2 were stable upon storage, whereas the composition of comparative example a phase separated to form a gel with coalescence of the silicone particles.

What is claimed is:

1. A hair styling composition comprising:
   (i) from 0.1% to 10% by weight, based on total weight, of a cross-linked silicone polymer, in which the percentage of branched monomer units in the silicone polymer is from 0.05% to 10%;
   (ii) from 0.1% to 10% by weight, based on total weight, of a cationic hair styling polymer having a cationic charge density of at least 1 meq/g;
   (iii) from 0.01% to 5% by weight, based on total weight, of a surfactant;
   (iv) water; and
   (v) from 0% to 30% by weight, based on total weight, of an aerosol propellant;
   wherein the cross-linked silicone polymer does not form a separate high viscosity aggregated phase.

2. A hair styling composition according to claim 1, in which the cross-linked silicone polymer (i) is a cross-linked dimethiconol, having a percentage of branched monomer units in the silicone polymer in the range 0.15% to 7%.

3. A hair styling composition according to claim 1, in which the cationic hair styling polymer (ii) has a cationic charge density of at least 2 meq/g and is selected from the group consisting of Polyquaternium 16, and vinylcaprolactam/vinylpyrrolidone/vinylimidazolium copolymers.

4. A hair styling composition according to claim 1, in which the cationic hair styling polymer (ii) has a cationic charge density from 2.8 to 7.0 meq/g.

5. A hair styling composition according to claim 1, which further comprises an alcohol selected from the group consisting of straight or branched chain monohydric alcohols having 2 to about 4 carbon atoms.

6. A hair styling composition according to claim 1 which is an aerosol hair mousse in which the level of propellant (v) is from 2% to 30% by weight, based on total weight.

7. A hair styling composition according to claim 6 in which the propellant (v) is a hydrocarbon propellant selected from the group consisting of propane, n-butane, isobutane and mixtures thereof.

8. A hair styling composition according to claim 1, which is a hair styling cream or gel including from 0.1% to 10% by weight based on total weight of a structurant or thickener.

* * * * *